(12) United States Patent
Falck-Pedersen et al.

(10) Patent No.: US 7,261,885 B2
(45) Date of Patent: Aug. 28, 2007

(54) ADENOVIRAL VECTOR WITH REPLICATION-DEPENDENT TRANSGENE EXPRESSION

(75) Inventors: Erik S. Falck-Pedersen, Dobbs Ferry, NY (US); Jason G. D. Gall, Germantown, MD (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 10/911,957

(22) Filed: Aug. 5, 2004

(65) Prior Publication Data

US 2005/0063953 A1     Mar. 24, 2005

Related U.S. Application Data

(63) Continuation of application No. PCT/US03/01507, filed on Jan. 17, 2003.

(60) Provisional application No. 60/354,785, filed on Feb. 5, 2002.

(51) Int. Cl.
*A61K 48/00*     (2006.01)
*C12N 15/861*    (2006.01)

(52) U.S. Cl. .................. 424/93.2; 435/320.1; 435/69.1

(58) Field of Classification Search ..................... None
See application file for complete search history.

(56) References Cited

U.S. PATENT DOCUMENTS

| 5,543,328 | A | 8/1996 | McClelland et al. |
| 5,677,178 | A | 10/1997 | McCormick |
| 6,020,172 | A | 2/2000 | Both |
| 6,127,525 | A | 10/2000 | Crystal et al. |
| 2003/0108524 | A1* | 6/2003 | Diagana et al. ............ 424/93.2 |
| 2005/0175589 | A1* | 8/2005 | Iggo et al. ................. 424/93.2 |
| 2005/0260162 | A1* | 11/2005 | Fueyo et al. ............... 424/93.2 |

FOREIGN PATENT DOCUMENTS

WO     WO99/55365 A     11/1999

OTHER PUBLICATIONS

Johnson et al, Selectively replicating adenoviruses targeting deregulated E2F activity are potent, systemic antitumor agents, Cancer Cell, May 2002, vol. 1, pp. 325-337.*
Hawkings et al, Gene Delivery from the E3 region of replicating human adenovirus; evaluation of the 6.7 K/gp 19 K region, Gene Therapy, 2001, vol. 8, pp. 1123-1131.*
Berk et al., *Ann. Rev. Genet.*, 20, 45-79 (1986).
Nevins et al., *Adv. Virus Res.*, 26 1-35 (1981).
Prescott et al., *Mol. Cell. Biol.*, 17 (4), 2207-2216 (1997).

* cited by examiner

*Primary Examiner*—Scott D. Priebe
*Assistant Examiner*—Maria Marvich
(74) *Attorney, Agent, or Firm*—Leydig, Voit & Mayer, Ltd.

(57) ABSTRACT

The invention provides an adenoviral vector comprising (a) at least a portion of an adenoviral genome comprising a major late transcription unit containing a terminal exon, wherein the terminal exon comprises a 5' splice acceptor DNA sequence element and a 3' polyadenylation signal sequence, and (b) a non-native nucleic acid sequence encoding a protein that does not contribute to the adenoviral vector entry into a host cell, wherein the non-native nucleic acid sequence is positioned within the terminal exon, such that the non-native nucleic acid sequence is selectively expressed in cells within which the adenoviral vector can replicate. The invention further provides an adenoviral vector composition and a method for treating or preventing a pathologic state in a mammal, comprising administering to the mammal the adenoviral vector composition of the invention in an amount sufficient to treat or prevent the pathologic state in the mammal.

19 Claims, No Drawings

ADENOVIRAL VECTOR WITH REPLICATION-DEPENDENT TRANSGENE EXPRESSION

CROSS-REFERENCE TO RELATED PATENT APPLICATIONS

This patent application is a continuation of copending International Patent Application No. PCT/US03/01507, filed Jan. 17, 2003, which designates the United States, and which claims the benefit of U.S. Provisional Patent Application No. 60/354,785, filed Feb. 5, 2002.

STATEMENT AS TO RIGHTS TO INVENTIONS MADE UNDER FEDERALLY SPONSORED RESEARCH AND DEVELOPMENT

This invention was made with Government support under Grant Number PO1HL57146 awarded by the National Institutes of Health. The United States Government may have certain rights in this invention.

TECHNICAL FIELD OF THE INVENTION

The present invention pertains to adenoviral vectors, as well as a method of using the same to treat or prevent a pathologic state in a mammal.

BACKGROUND OF THE INVENTION

By convention, the adenovirus life cycle is divided into two phases, the early and the late phase, which are separated by the onset of viral DNA replication and characterized by the expression of specific subsets of the viral genome. In the early phase, the early genes E1, E2, E3, and E4 are maximally expressed (E1b, E2, E3, and E4 expression being activated by the immediate early gene E1a (see, e.g., Berk et al., *Annu. Rev. Genet.*, 20:45-79 (1986)), and the major late transcription unit (MLTU) is expressed at very low levels and is attenuated. At the onset of viral DNA replication, a marked switch in gene expression occurs, resulting in the reduction of expression of the early genes and an increase in activation of the late genes, most of which are translated from mRNAs originating from the MLTU.

The MLTU is 25 kB in length and contains six polyadenylation (polyA) sites, five that are unique to the MLTU (L1 through L5) and one used by both the E3 transcription unit and the MLTU (see, e.g., Prescott et al., *Mol. and Cell. Biol.*, 17(4):2207-2216 (1997)). Each polyA site is associated with several potential splice acceptors, and all 5' terminal exons are spliced to a common tripartite leader (see, e.g., Nevins et al., *Adv. Virus Res.*, 26:1-35 (1981)). Due to complex alternative RNA splicing, each late region produces multiple mRNAs. Indeed, during the late stage of adenovirus infection, all six polyA sites are used in conjunction with a variety of splice acceptors to produce a minimum of 45 different mature mRNAs. The extremely high level of mRNA production and the novel splicing/polyadenylation capacity of the MLTU are essential to the production of adenoviral virions.

Recombinant adenoviral vectors characterized as having a whole or partial deletion of one or more early region genes have been extensively studied. Many of these recombinant adenoviral vectors are engineered to contain a nucleic acid sequence encoding a therapeutic factor prior to being delivered to a population of cells for gene therapy. Limitations remain, however, for the production of an adenoviral vector able to carry out its effects (e.g., to deliver a therapeutic factor) only in certain cell types (e.g., cancer cells). Progress has been made with these limitations in mind by employing a number of different approaches. Some of these approaches have investigated inserting non-native ligands, or nucleic acid sequences encoding such ligands, into the MLTU, which theoretically allows for these adenoviral vectors to bind specific cell surface receptors to which it may not normally bind. For example, International (PCT) Patent Application WO 99/55365 describes an adenoviral vector comprising a first non-native nucleic acid sequence and a second non-native nucleic acid sequence which is different from the first non-native nucleic acid sequence. The first non-native nucleic acid sequences encodes, for example, a chimeric fiber protein that does not bind to the native adenoviral fiber receptor known as the Coxsackievirus-Adenovirus Receptor (CAR) but will bind to a receptor present on the surface of a target cell of interest. The fiber protein which binds to a receptor present on the surface of a target cell can be placed at any suitable location within the adenoviral genome, including 3' of the L5 polyA site. This fiber protein also comprises splice acceptor elements and 3' polyA signals.

Similarly, U.S. Pat. No. 5,543,328 describes an adenovirus comprising a fiber protein comprising a ligand, which is specific for a receptor located on a desired cell type. The ligand either replaces a portion of the fiber protein, or the adenovirus includes a fusion protein composed of the adenovirus fiber protein and the ligand. In certain embodiments, the ligand can be a tumor necrosis factor (TNF), transferrin, ApoB, α-2-macroglobulin, α-1 acid glycoprotein, mannose-containing peptide, sialyl-Lewis-X antigen-containing peptide, CD34 ligand, CD40 ligand, ICAM-1, M-CSF, circumsporozoite protein, VLA-4, LFA-1, NGF, HIV gp120, Class II MHC antigen, colony stimulating factor (CSF), insulin-like growth factor, or Interleukins 1 through 14. The adenovirus also can include a gene(s) encoding a therapeutic factor(s), which is typically inserted into the E1 or E3 region of the adenovirus.

In other approaches, a nucleic acid sequence encoding a therapeutic factor or ligand is not included in the adenoviral genome at all. For example, U.S. Pat. No. 5,677,178 (Mc-Cormick-Onyx Pharmaceuticals) describes the use of a certain type of replication-deficient adenovirus that replicates in certain abnormal (i.e., cancer) cells but does not replicate in normal (i.e., non-cancerous) cells. The conditionally replication-deficient adenovirus kills the abnormal cells through the expression of a replicative phenotype wherein the abnormal cells are lysed as part of the viral replication process. Thus, the adenovirus is replication-deficient in normal cells but is replication competent in abnormal cells.

To achieve this selective replication, the adenoviral vector described in the '178 patent substantially lacks an expressed viral oncoprotein capable of binding a functional p53 tumor suppressor gene product and/or a functional Rb tumor suppressor gene product. Abnormal cells lacking a functional p53 tumor suppressor gene product and/or a functional Rb tumor suppressor gene product can support the replication of the otherwise replication-deficient adenovirus substantially lacking an expressed viral oncoprotein capable of binding a functional p53 tumor suppressor gene product and/or functional Rb tumor suppressor gene product, respectively.

While previously-described vectors have been somewhat effective at delivering nucleic acids to target cells or treating certain disease states, a need remains to provide an adenoviral vector which more selectively carries out its activities in target cells, i.e., cells responsible for certain disease states, such that these adenoviral vectors can be formulated into therapeutic compositions and used in methods of treating these disease states. The invention provides such a vector, composition, and method. These and other advantages of the invention, as well as additional inventive features, will be apparent from the description of the invention provided herein.

SUMMARY OF THE INVENTION

The invention provides an adenoviral vector comprising at least a portion of an adenoviral genome comprising a MLTU containing a terminal exon, wherein the terminal exon comprises a 5' splice acceptor DNA sequence element, a 3' polyadenylation (polyA) signal sequence, and a non-native nucleic acid sequence encoding a protein that does not contribute to the adenoviral vector entry into a host cell. The non-native nucleic acid sequence is positioned within the terminal exon such that the non-native nucleic acid sequence is selectively expressed in cells within which the adenoviral vector can replicate. The invention further provides an adenoviral vector composition comprising an adenoviral vector of the invention and a carrier. Moreover, the invention provides a method for treating or preventing a pathologic state in a mammal, wherein the pathologic state is characterized by the presence of abnormal cells. The method comprises administering to the mammal an adenoviral vector composition of the invention in an amount sufficient to treat or prevent the pathologic state in the mammal, wherein the adenoviral vector replicates in the abnormal cells and the non-native nucleic acid sequence is selectively expressed in the abnormal cells, whereupon the pathologic state in the mammal is treated or prevented.

DETAILED DESCRIPTION OF THE INVENTION

The invention is predicated, at least in part, on the fact that several DNA viruses which infect mammalian cells (e.g., adenoviruses; papovaviruses such as BK and JC; SV40; and papillomaviruses such as HPV) encode viral proteins which are essential for efficient progression through the viral replication cycle. Some of these viral proteins sequester cellular proteins, such as those involved in cell-cycle control and/or formation of transcription complexes, as a necessary condition for efficient viral replication. In the absence of the viral proteins which bind, sequester, or degrade such cellular proteins (e.g., p53 and retinoblastoma (Rb)), viral replication is substantially inhibited. Therefore, normal cells which are infected with a mutant virus lacking such viral proteins are generally unable to support replication of the mutant virus. However, since the sequestration or degradation of p53 or Rb is not necessary for viral replication in cells which lack functional p53 or Rb, it is possible that mutant viruses, which are defective for the viral proteins which interact with p53, Rb, and other cellular gene products which influence viral replication sequestration or degradation, may replicate in cells lacking such cellular gene products to a greater extent than in cells having essentially normal function. Abnormal cells (e.g., cancer cells) frequently lack these cellular gene products. Hence, the adenoviral vectors of the invention preferentially replicate in abnormal cells as compared to normal cells.

In view of the above, the invention provides an adenoviral vector comprising (a) at least a portion of an adenoviral genome comprising a major late transcription unit (MLTU) containing a terminal exon, wherein the terminal exon comprises a 5' splice acceptor DNA sequence element and a 3' polyadenylation (polyA) signal sequence, and (b) a non-native nucleic acid sequence encoding a protein that does not contribute to the adenoviral vector entry into a host cell, wherein the non-native nucleic acid sequence is positioned within the terminal exon, such that the non-native nucleic acid sequence is selectively expressed in cells within which the adenoviral vector can replicate. Because the MLTU is active upon viral replication, the non-native nucleic acid sequence will only be expressed when viral replication is allowed to proceed.

A "terminal exon" is defined herein as a region contained in the MLTU that comprises a nucleic acid sequence encoding a protein (e.g., an open reading frame), a 5' splice acceptor site, and a 3' polyA processing site. Late regions L1-L5 are each normally contained in the MLTU in separate terminal exons. The invention involves the design and subsequent insertion of a terminal exon comprising a non-native nucleic acid sequence into the MLTU, or, alternatively, involves modifying an existing terminal exon already contained in the MLTU to comprise a non-native nucleic acid sequence.

In the context of the invention, the adenoviral vector can be derived from any serotype of adenovirus. Adenoviral stocks that can be employed as a source of adenovirus can be amplified from the adenoviral serotypes 1 through 51, which are currently available from the American Type Culture Collection (ATCC, Manassas, Va.), or from any other serotype of adenovirus available from any other source. For instance, an adenovirus can be of subgroup A (e.g., serotypes 12, 18, and 31), subgroup B (e.g., serotypes 3, 7, 11, 14, 16, 21, 34, and 35), subgroup C (e.g., serotypes 1, 2, 5, and 6), subgroup D (e.g., serotypes 8, 9, 10, 13, 15, 17, 19, 20, 22-30, 32, 33, 36-39, and 42-47), subgroup E (serotype 4), subgroup F (serotypes 40 and 41), or any other adenoviral serotype. The adenovirus preferably is of group C, particularly of serotype 2 or 5. Adenoviral vectors, methods of producing adenoviral vectors, and methods of using adenoviral vectors are disclosed in, for example, U.S. Pat. Nos., 5,851,806 and 5,994,106, and International Patent Applications WO 95/34671 and WO 97/21826. However, non-group C adenoviruses can be used to prepare adenoviral vectors for delivery of one or more non-native nucleic acid sequences to a desired tissue. Preferred adenoviruses used in the construction of non-group C adenoviral vectors include Ad12 (group A), Ad7 (group B), Ad9, Ad30, and Ad36 (group D), Ad4 (group E), and Ad41 (group F). Non-group C adenoviral vectors, methods of producing non-group C adenoviral vectors, and methods of using non-group C adenoviral vectors are disclosed in, for example, U.S. Pat. Nos. 5,801,030; 5,837,511; and 5,849,561 and International Patent Applications WO 97/12986 and WO 98/53087.

In preferred embodiments, the adenoviral vector of the invention is deficient in one or more replication-essential gene functions. Replication-essential gene functions include regions contained within the adenoviral genome which are necessary for viral DNA replication, such as E1a, E1b, E2, E4, as well as regions necessary for viral propagation, such as L1-L5. By "deficient" is meant a disruption contained within at least one of the above-mentioned regions such that the wild-type gene product encoded by the region is produced in a reduced amount as compared to normal levels. The disruption can be, for example, a point mutation, substitution, deletion, insertion and/or inversion. Preferably, the adenoviral vector is deficient in one or more replication-essential gene functions of the E1a, E1b, and/or E4 regions.

Accordingly, the invention provides an adenoviral vector that can be deficient in one or more replication-essential gene functions of the E1a region but can retain the one or more replication-essential gene functions of the E1b and/or E4 regions. Such an adenoviral vector selectively replicates in, for example, cells lacking a functional Rb gene product. Alternatively, the adenoviral vector can be deficient in the one or more replication-deficient gene functions of the E1b region but can retain the one or more replication-essential gene functions of the E1a and/or E4 regions. Such an adenoviral vector selectively replicates in, for example, cells lacking a functional p53 gene product. In another embodiment, the adenoviral vector can be deficient in the one or more replication-deficient gene functions of each of the E1a and E1b regions and will typically include further deletions of the E4 region. When these adenoviral vectors contain deletions in the E4 region, ORF6 of the E4 region will be included in a terminal exon which will allow for these adenoviral vectors to substantially replicate in, for example, cells lacking a functional p53 and Rb gene product. Preferably, such an adenoviral vector will be deficient in the E3 region and will include a nucleic acid sequence encoding a therapeutic factor useful in treating a pathologic state in place of the E3 region.

Although the cellular factors with which viral proteins interact are described herein in the context of p53 and Rb, it will be understood that p53 and Rb only represent examples of known cellular proteins potentially involved in the viral replication cycle. As such, the invention is not limited to adenoviral vectors that selectively replicate in cells lacking normal p53 and Rb function. Indeed, the adenoviral vectors of the invention can be engineered to interact or to prevent interaction with any cellular protein, either known or unknown, which influences the replication of the adenoviral vector and thus promotes adenoviral replication only in a specific subset of cells by altering regions other than E1a and E1b of the adenoviral genome. Accordingly, the adenoviral vectors and the abnormal cells for which these vectors can replicate, as they are described herein, are in no way limiting.

Normally, the adenoviral E1b 55 kd gene product forms a complex with the host cell p53 protein, thereby sequestering and/or inactivating p53 and allowing viral replication to proceed. Without an E1b 55 kd gene product and its interaction with p53, viral replication is substantially inhibited. However, adenoviral vectors lacking a functional E1b 55 kd gene product are able to replicate in cells lacking p53, since the lack of p53 renders its sequestration unnecessary for viral replication to occur in these abnormal cells. In view of the above, an adenoviral vector of the invention can comprise an E1b locus encoding a mutant 55 kd protein that is substantially incapable of forming a functional complex with p53 in infected cells. The substantial incapacity of the adenoviral vector to effectively sequester p53 in infected normal cells results in the introduced recombinant adenoviral vector failing to replicate in these cells. By contrast, infected abnormal cells which lack a functional p53 protein support replication of the introduced adenoviral vector. Thus, the non-native nucleic acid sequence contained in the MLTU is expressed in these abnormal cells but remains silent in the infected normal cells.

Suitable adenoviral vectors which lack the ability to interact with p53 for use in the present invention include, but are not limited to, (1) adenovirus type 2 dl 1520, which contains a C to T mutation at nucleotide position 2022 that generates a stop codon 3 amino acids downstream of the AUG codon used for initiation of translation of the 55 kd protein and a deletion between nucleotides 2496 and 3323 replaced with a small linker insertion that generates a second stop codon at nucleotide 3336, with the expression of the p19 protein being essentially unaffected (see, e.g., Barker and Berk, *Virology*, 156: 107 (1987)), and (2) a composite adenovirus construct comprising adenovirus type 2 dl 1520 comprising at least the position 2022 mutation and/or the 2496-3323 deletion mutation, or a substantial portion thereof, and an additional mutation in p19 to yield a p19 cyt mutant, with the composite virus construct lacking the nucleic acid sequence encoding the 55 kd protein and comprising the enhanced cytopathic effect of the p19 cyt mutation.

Similar to the above, the adenoviral E1a gene product (e.g., p289R or p243R) forms a complex with the host cell Rb protein, thereby sequestering and/or inactivating Rb. Without an E1a gene product and its interaction with Rb, viral replication is substantially inhibited. However, adenoviral vectors lacking a functional E1a gene product are able to replicate in cells lacking Rb, since the lack of Rb renders its sequestration unnecessary for viral replication to occur in these abnormal cells. In view of the above, an adenoviral vector of the invention can comprise an E1a locus encoding an E1a protein (e.g., p289R or p243R) that is substantially incapable of forming a complex with Rb in infected cells. The substantial incapacity of the adenoviral vector to effectively sequester Rb protein in infected normal cells results in the introduced adenoviral vector failing to replicate in these cells. By contrast, infected abnormal cells which lack a functional Rb protein support replication of the introduced adenoviral vector. Thus, the non-native nucleic acid sequence contained in the MLTU is expressed in these abnormal cells but remains silent in the infected normal cells. In preferred variations of these embodiments, the adenoviral vector comprises an E1a locus encoding a mutant E1a protein (e.g., p289R) that lacks a CR1 and/or CR2 domain capable of binding Rb (and/or the 300 kD polypeptide and/or the 107 kD polypeptide) but comprises a functional CR3 domain capable of transactivation of adenoviral early genes. Additional variations of these embodiments include those where the adenoviral vector comprises a nonfunctional E1a locus which is substantially incapable of expressing a protein that binds to and inactivates Rb and may optionally also comprise a functional p19 protein (i.e., capable of stimulating expression of adenoviral early region genes in the absence of E1a function).

Suitable adenoviral vectors which lack the ability to interact with Rb for use in the invention include, but are not limited to, (1) adenovirus serotype 5 NT dl 1010, which encodes an E1a protein lacking the CR1 and CR2 domains (deletion of amino acids 2 to 150; nucleotides 560-1009) necessary for efficient Rb binding, but substantially retaining the CR3 domain (see, e.g., Whyte et al., *Cell*, 56: 67 (1989)), and (2) adenovirus serotype 5 dl 312, which comprises a deleted viral genome lacking the region spanning nucleotides 448-1349 which encodes the entire E1a region in wild-type adenovirus (see, e.g., Jones and Shenk, *PNAS*, 76: 3665 (1979)).

Additional adenoviral vectors lacking the capacity to bind p53, Rb, and/or other cellular proteins which influence the replication of the adenoviral vector can be produced by those of skill in the art by generating mutations in a region of the adenoviral genome encoding a polypeptide; expressing the mutant polypeptide; contacting the mutant polypeptide with p53, Rb, or other desired cellular protein, or a binding fragment of any of the above, under suitable binding conditions; and identifying mutant polypeptides which do not specifically bind the desired cellular protein or protein fragment as being candidate regions to alter in order to produce adenoviral vectors suitable for use in the invention. Alternative functional and/or binding assays can be used to identify adenoviral vectors suitable for use in the invention and are described in, for example, Frebourg et al., *Cancer Res.*, 52(24):6976-6978 (1992), and Chellappan et al., *PNAS*, 89(10):4549-4553 (1992).

Adenoviral vectors of the invention also can lack the capacity to bind p53 as well as the capacity to bind Rb. Such adenoviral vectors will preferentially replicate in $p53^{(-)}$ $Rb^{(-)}$ cells and can be constructed by those of skill in the art by combining a mutation in the E1a region and a mutation in E1b region encoding 55 kd. For example, the Ad5 dl 434 mutant (see, e.g., Grodzicker et al., *Cell*, 21(2):454-463 (1980)) comprises a deletion of the E1a locus and a partial deletion of the E1b locus, and substantially lacks the capacity to encode functional E1a and E1b 55 kd proteins.

In view of the above, adenoviral vectors lacking the capacity to express a functional Rb inactivating protein (e.g., adenovirus E1a) will preferentially replicate in $Rb^{(-)}$ cells and $Rb^{(-)}$ $p53^{(-)}$ cells. Viral mutants lacking the capacity to express a functional p53 inactivating protein (e.g., adenovirus E1b 55 kd) will preferentially replicate in $p53^{(-)}$ cells and $Rb^{(-)}$ $p53^{(-)}$ cells. Viral mutants lacking the capacity to express both a functional p53 inactivating protein and a functional Rb inactivating protein will preferentially replicate in $Rb^{(-)}$ $p53^{(-)}$ cells. Although some replicating normal cells may transiently exhibit a $Rb^{(-)}$ phenotype, $p53^{(-)}$ phenotype, or $Rb^{(-)}$ $p53^{(-)}$ phenotype during progression through the cell cycle, the viral mutants of the invention may be used for the preferential killing of abnormal cells, thus constituting a useful cancer therapy to be used alone or in combination with other methods of treatment. Moreover, as mentioned above, the adenoviral vectors of the invention can be engineered to interact or to prevent interaction with other cellular proteins, either known or unknown, that influence viral replication.

It may be desirable to incorporate additional mutations into any of the above described adenoviral vectors. Such mutations can include mutations within the E1a, E1b, E2, E3, E4, L1, L2, L3, L4, and/or L5 regions so long as the adenoviral vector selectively replicates in a desired subset of cells.

The replication of the adenoviral vector in an infected cell correlates with viral-induced cytotoxicity, generally by cell lysis, cytopathic effect (CPE), apoptosis, or other mechanisms of cell death. The inclusion of the non-native nucleic acid sequence in the MLTU typically augments the cytotoxicity of the adenoviral vector. The non-native nucleic acid sequence contained in the MLTU of the adenoviral vector can encode any suitable protein and is positioned within a terminal exon, such that the non-native nucleic acid sequence is selectively expressed in cells within which the adenoviral vector can replicate. By "non-native" is meant any nucleic acid sequence which is either not normally present in the adenoviral genome or which is normally present but has been removed and placed in a different location from where it originated. The non-native nucleic acid sequence encodes a protein that does not contribute to the adenoviral vector entry into a host cell. Proteins that contribute to viral entry include, for example, various ligands or other surface proteins, which have the ability to recognize specific cell surface receptors on a particular cell type (e.g., cancer cells). These proteins are well known in the art and are described in, for example, International (PCT) Application WO 99/55365, International (PCT) Application WO 96/26281, and U.S. Pat. No. 5,543,328.

Preferably, the non-native nucleic acid sequence encodes a protein that initiates an immune response against the cells within which the adenoviral vector can replicate when the cells are in a mammal. Non-native nucleic acid sequences encoding cytokines are particularly preferred to initiate such an immune response. Examples of cytokines include, but are not limited to, interleukins, interferons (i.e., INF-α, INF-b, INF-γ), leukemia inhibitory factor (LIF), oncostatin M (OSM), granulocyte-macrophage colony stimulating factor (GM-CSF), granulocyte colony stimulating factor (G-CSF), tumor necrosis factor-alpha (TNF-α), tumor necrosis factor-beta (TNF-b), and transforming growth factor-beta (TGF-b). Preferably, the cytokine is selected from the group consisting of an interleukin, an interferon and a tumor necrosis factor. Alternatively, the non-native nucleic acid sequence can encode a protein that is toxic to the cells within which the adenoviral vector replicates and/or other cells (e.g., cells in the vicinity of the cells within which the adenoviral vector replicates). In this respect, the non-native nucleic acid sequence can encode an apoptotic factor (e.g., Bax, Bak, Bcl-$X_5$, Bad, Bim, Bik, Bid, Harakiri, ICE-CED3 proteases, TRAIL, SARP-2, apoptin); an enzyme (e.g., cytosine deaminase, adenosine deaminase, hypoxanthine-guanine phosphoribosyltransferase, and thymidine kinase); a toxin (e.g., ricin A-chain, diphtheria toxin A, pertussis toxin A subunit, *E. coli* enterotoxin A subunit, cholera toxin A subunit and pseudomonas toxin c-terminal); an antisense molecule; a ribozyme; or a cell cycle regulator (e.g., p27, p21, p57, p18, p73, p19, p15, E2F-1, E2F-2, E2F-3, p107, p130 and E2F-4).

In another embodiment, the non-native nucleic acid sequence can encode a gene product normally found in an adenoviral genome, such as an early region gene, that has been removed from its original location and placed in a terminal exon. For example, the ORF6 of the E4 region can be removed and placed in a terminal exon contained in the MLTU, rendering such adenoviral vectors replication deficient in cells for which the MLTU remains silent. An adenoviral vector deficient in one or more replication-essential gene functions of the E1a, E1b, and E4 regions and containing a terminal exon comprising ORF6 of the E4 region has the ability to replicate in 293 cells, which normally do not support replication of an adenoviral vector without an alternative source providing E4 function (e.g., a helper virus). Typically, such adenoviral vectors also are deficient in E3 and can thus contain an additional non-native nucleic acid sequence in either of the E1 or E3 regions.

The non-native nucleic acid sequence can be inserted at any suitable position in any terminal exon contained in the MLTU. For example, the terminal exon comprising the non-native nucleic acid sequence can be located either upstream or downstream of the L1 region of the terminal exon. By "upstream" is meant 5' of the splice acceptor region contained in the terminal exon. By "downstream" is meant 3' of the polyA site contained in the terminal exon. Preferably, the terminal exon comprising the non-native nucleic acid sequence is located downstream of the L3 region, and, more preferably, downstream of the L5 region. Also preferably, the terminal exon comprising the non-native nucleic acid sequence is contained in the MLTU in a location that does not perturb any adenoviral transcript or reading frame.

As mentioned above, it is envisioned that the non-native nucleic acid sequence can be contained in the terminal exon in a number of different arrangements. For example, the terminal exon can comprise from 5' to 3': (a) a 5' splice acceptor DNA sequence element, (b) a non-native nucleic acid sequence, and (c) a 3' polyA sequence. Alternatively, the terminal exon can comprise from 5' to 3': (a) a 5' splice acceptor DNA sequence element, (b) a native nucleic acid sequence, (c) an internal ribosomal entry site (IRES), (d) a non-native nucleic acid sequence, and (e) a 3' polyA sequence, such that both the native and non-native nucleic acid sequences are expressed in cells within which the adenoviral vector can replicate. In regards to the latter embodiment, the native nucleic acid sequence typically will encode a gene product produced by one of regions L1-L5 and will be located in its natural position within the adenoviral genome. Also, the use of an IRES allows for each open reading frame to be accessible to ribosomes for efficient translation. In this respect, multiple genes can be efficiently expressed using a single promoter/enhancer to transcribe a single message (see, e.g., U.S. Pat. Nos. 5,925,565 and 5,935,819)

Any number of terminal exons can be included in the adenoviral vector of the invention. Although only one terminal exon comprising a non-native nucleic acid sequence is sufficient to obtain the desired effect, it is envisioned that the MLTU can contain multiple terminal exons, each comprising the same or different non-native nucleic acid sequence. For example, the adenoviral vector can comprise a MLTU containing one terminal exon comprising a non-native nucleic acid sequence encoding a protein which initiates an immune response against the cells within which the adenoviral vector can replicate and a second terminal exon, located either upstream or downstream of the first terminal exon, comprising a non-native nucleic acid sequence encoding a protein that is toxic to the cells within which the adenoviral vector can replicate. Alternatively, the adenoviral vector can be deficient in one or more replication-essential gene functions of the E1a, E1b, and E4 regions and can comprise a MLTU containing one terminal exon comprising a non-native nucleic acid sequence encoding ORF6 of the E4 region and a second terminal exon, located either upstream or downstream, comprising a non-native nucleic acid sequence encoding a protein which augments the cytotoxicity of the adenoviral vector towards cells within which the adenoviral vector can replicate.

In addition, the adenoviral vector can further comprise one or more transgenes contained in any suitable region outside the MLTU. By "transgene" is meant any nucleic acid molecule that can be expressed in a cell (i.e., the nucleic acid molecule is operably linked to a promoter). Desirably, the expression of the transgene is beneficial, e.g., prophylactically or therapeutically beneficial, to the pathologic state for which treatment is being given. If the transgene confers a prophylactic or therapeutic benefit to the cell, the transgene can exert its effect at the level of RNA or protein. For example, the transgene can encode a peptide, other than the protein encoded by the non-native nucleic acid sequence, that can be employed in the treatment or study of a disorder, e.g., cancer. Alternatively, the transgene can encode an antisense molecule, a ribozyme, a protein that affects splicing or 3' processing (e.g., polyadenylation), or a protein that affects the level of expression of another gene within the cell (i.e., where gene expression is broadly considered to include all steps from initiation of transcription through production of a process protein), such as by mediating an altered rate of mRNA accumulation or transport or an alteration in post-transcriptional regulation. The transgene can encode a chimeric peptide for combination treatment of a pathologic state.

A nucleic acid sequence encoding a marker protein, such as green fluorescent protein or luciferase also can be present in the adenoviral vector. Such marker proteins are useful in vector construction and determining vector migration. Marker proteins also can be used to determine points of injection in order to efficiently space injections of an adenoviral vector composition to provide a widespread area of treatment, if desired. Alternatively, a nucleic acid sequence encoding a selection factor, which also is useful in vector construction protocols, can be part of the adenoviral vector.

Negative selection genes can be incorporated into any of the above-described adenoviral vectors. A preferred embodiment is an HSV tk gene cassette (Zjilstra et al., Nature, 342: 435 (1989); Mansour et al., Nature, 336: 348 (1988); Johnson et al., Science, 245: 1234 (1989): Adair et al., PNAS, 86: 4574 (1989); Capecchi, Science, 244: 1288 (1989)) operably linked to the E2 promoter. The tk expression cassette (or other negative selection expression cassette) is inserted into the adenoviral genome, for example, as a replacement for a substantial deletion of the E3 gene. Other negative selection genes will be apparent to those of skill in the art. It is believed that a negative selection gene operably linked to the E2 promoter is an especially preferred embodiment for incorporation into E1a$^{(-)}$ adenoviral vectors, as the E2 promoter contains multiple E2F sites, whereas Rb$^{(-)}$ and p53$^{(-)}$ Rb$^{(-)}$ lack Rb function and presumably will exhibit more efficient transcription from the E2 promoter.

An adenoviral vector of the invention desirably is formulated and administered to a mammal in an adenoviral vector composition. Such adenoviral vector compositions typically comprise an adenoviral vector and a carrier. Preferably, the carrier is a pharmaceutically (e.g., physiologically) acceptable carrier and can be used within the context of the present invention. Such carriers are well known in the art. The choice of carrier will be determined, in part, by the particular site to which the composition is to be administered and the particular method used to administer the adenoviral vector composition.

Suitable formulations include aqueous and non-aqueous solutions, isotonic sterile solutions, which can contain antioxidants, buffers, bacteriostats, and solutes that render the formulation isotonic with the blood or intraocular fluid of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. When administering an adenoviral vector composition, preferably the pharmaceutically acceptable carrier is a buffered saline solution. More preferably, the adenoviral vector composition for use in the present inventive methods is administered in an adenoviral vector composition formulated to protect the adenoviral vector from damage prior to administration. For example, the adenoviral vector composition can be formulated to reduce loss of the adenoviral vector on devices used to prepare, store, or administer the adenoviral vector composition, such as glassware, syringes, or needles. The adenoviral vector composition can be formulated to decrease the light sensitivity and/or temperature sensitivity of the adenoviral vector itself. To this end, the adenoviral vector composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof (see, e.g., U.S. Pat. No. 6,225,289). Use of such an adenoviral vector composition will extend the shelf life of the adenoviral vector composition, facilitate administration, and increase the effectiveness of the adenoviral vector. In this regard, an adenoviral vector composition also can be formulated to enhance transduction efficiency.

In addition, the adenoviral vector composition of the invention can encode, or alternatively can be administered in conjunction with, other therapeutic or biologically active agents. For example, non-native nucleic acid sequences useful in the treatment of a particular indication can be present. Alternatively, or, additionally, when treating cancer, other anticancer compounds can be used in conjunction with the composition of the invention and can include, but are not limited to, all of the known anticancer compounds approved for marketing in the United States and those that will become approved in the future. See, for example, Table 1 and Table 2 of Boyd, Current Therapy in Oncology, Section 1. Introduction to Cancer Therapy (J. E. Niederhuber, ed.), Chapter 2, by B.C. Decker, Inc., Philadelphia, 1993, pp. 11-22. More particularly, these anticancer compounds include doxorubicin, bleomycin, vincristine, vinblastine, VP-16, VW-26, cisplatin, carboplatin, procarbazine, and taxol for solid tumors in general; alkylating agents, such as BCNU, CCNU, methyl-CCNU and DTIC, for brain or kidney cancers; and antimetabolites, such as 5-FU and methotrexate, for colon cancer.

Accordingly, the invention provides a method for treating or preventing a pathologic state in a mammal, wherein the pathologic state is characterized by the presence of abnormal cells, comprising administering to the mammal an adenoviral vector composition, as described herein, in an amount sufficient to treat or prevent the pathologic state in the mammal, wherein the adenoviral vector replicates in the abnormal cells and the non-native nucleic acid sequence is selectively expressed in the abnormal cells, whereupon the pathologic state in the mammal is treated or prevented.

"Abnormal cells" as they are described herein, refer to cells which do not have a normal cellular function. Typically, the loss of a normal cellular function will be attributed to a decreased level of a wild-type cellular protein that normally has the ability to associate with an adenoviral gene product. For example, cells which lack normal expression levels of p53 are considered abnormal in the context of the invention. An accumulation of abnormal cells can be involved in the progression of a particular pathologic state (e.g., cancer).

The pathologic state can be any pathologic state that is characterized by the presence of abnormal cells, e.g., that has resulted from the accumulation of abnormal cells. For example, the pathologic state can be cancer, and the abnormal cells can be cancer cells. Human tumor cells frequently lack p53 and/or Rb function necessary for normal control of the cell cycle (Hollstein et al., *Science*, 253: 49 (1991); Levine et al., supra (1991)). Thus, many abnormal cells are $p53^{(-)}$, $Rb^{(-)}$, or deficient in both, either because they lack sufficient levels of the protein or because they express mutant forms of the protein which are incapable of normal function, and which may substantially diminish normal function even when the wild-type counterpart may be present (e.g., by inhibiting formation of functional multimers). Some abnormal cells may comprise alleles encoding essentially wild-type proteins, but may comprise a second site mutation that substantially abrogates normal function, such as a mutation that results in p53 protein being localized in the cytoplasm rather than in the nucleus. The non-native nucleic acid sequence desirably encodes a protein which is toxic to one or more different cancer cell types.

The pathologic state can be any type of cancer. Cancers can include lung cancer, colon cancer, renal cancer, anal cancer, bile duct cancer, bladder cancer, bone cancer, brain cancer, spinal chord cancer, breast cancer, cervical cancer, lymphoma, endometrial cancer, esophageal cancer, gallbladder cancer, gastrointestinal cancer, laryngeal cancer, leukemia, liver cancer, multiple myeloma, neuroblastoma, ovarian cancer, pancreatic cancer, prostatic cancer, retinoblastoma, skin cancer (e.g., melanoma and non-melanoma), stomach cancer, testicular cancer, thymus cancer, and thyroid cancer, as well as other carcinomas and sarcomas.

Other pathologic states are also contemplated in the context of the invention. For example, the pathologic state can be an inflammatory disease (e.g., arthritis), a neurodegenerative disease, a disease of an organ which is attributed to the presence of abnormal cells, or any other pathologic state for which the selective expression of a non-native nucleic acid sequence in abnormal cells will treat or prevent a particular pathologic state. Such embodiments will be achievable through routine experimentation by one of ordinary skill in the art.

Suitable methods, i.e., invasive and noninvasive methods, of directly administering an adenoviral vector composition, are available. Although more than one route can be used for administration, a particular route can provide a more immediate and more effective reaction than another route. The inventive method is not dependent on the mode of administering the adenoviral vector composition to a mammal, preferably a human, to achieve the desired effect. As such, any route of administration is appropriate so long as the adenoviral vector composition contacts and enters a cell within which the adenoviral vector can replicate. The adenoviral vector composition can be appropriately formulated and administered in the form of a local injection, lotion, ointment, implant, or the like. The adenoviral vector composition can be applied, for example, topically, intratumoraly, or peritumoraly. The adenoviral vector composition can be administered through multiple applications and/or multiple routes to ensure sufficient exposure of cells promoting adenoviral replication to the adenoviral vector composition.

The adenoviral vector composition can be administered using invasive procedures, such as, for instance, local injection (e.g., intratumoral injection). Intratumoral injections involve the administration of the adenoviral vector composition directly into a tumor cell(s), which desirably selectively allow for adenoviral replication. Pharmaceutically acceptable carriers for injectable compositions are well known to those of ordinary skill in the art (see Pharmaceutics and Pharmacy Practice, J.B. Lippincott Co., Philadelphia, Pa., Banker and Chalmers, eds., pages 238-250 (1982), and ASHP Handbook on Injectable Drugs, Toissel, 4th ed., pages 622-630 (1986)).

The adenoviral vector composition can be non-invasively administered to a mammal. For instance, if multiple surgeries have been performed, the mammal displays low tolerance to anesthetic, or other disorders exist, topical administration of the adenoviral vector composition may be most appropriate. Topical formulations are well known to those of skill in the art. An adenoviral vector composition also can be administered non-invasively using a needleless injection device, such as the Biojector 2000 Needle-Free Injection Management System® available from Bioject, Inc.

The adenoviral vector composition is preferably present in or on a device that allows controlled or sustained release, such as a biocompatible polymeric matrix, meshwork, mechanical reservoir, or mechanical implant. Implants (see, e.g., U.S. Pat. Nos. 5,443,505, 4,853,224 and 4,997,652), devices (see, e.g., U.S. Pat. Nos. 5,554,187, 4,863,457, 5,098,443 and 5,725,493), such as an implantable device, e.g., a mechanical reservoir or an implant or a device comprised of a polymeric composition, are particularly useful for the administration of the adenoviral vector composition. The adenoviral vector composition also can be administered in the form of a sustained-release formulation (see, e.g., U.S. Pat. Nos. 5,378,475) comprising, for example, gelatin, chondroitin sulfate, a polyphosphoester, such as bis-2-hydroxyethyl-terephthalate (BHET), or a polylactic-glycolic acid.

When administering the adenoviral vector composition, the appropriate dosage and route of administration can be selected to minimize loss of the adenoviral vector composition or inactivation of the adenoviral vector composition due to a host's immune system. For example, for contacting cells in vivo, it can be advantageous to administer to an immunosuppressive agent (e.g., cyclophosphamide or FK506) or monoclonal antibody that can block a T cell receptor, prior to performing the inventive method. Prior administration of an immunosuppressive agent or monoclonal antibody can serve to decrease the amount of adenoviral vector cleared by the immune system.

The dose of adenoviral vector composition administered to a mammal, particularly a human, in accordance with the invention should be in an amount sufficient to treat prophylactically or therapeutically a mammal for a pathologic state. Dosage will depend upon a variety of factors, including the age, species, the pathology in question, and condition or disease state. Dosage also depends on the non-native nucleic acid sequence, as well as the amount of tissue about to be affected or actually affected by the disease. The size of the dose also will be determined by the route, timing, and frequency of administration as well as the existence, nature, and extent of any adverse side effects that might accompany the administration of a particular adenoviral vector composition and the desired physiological effect. It will be appreciated by one of ordinary skill in the art that various conditions or disease states, in particular, chronic conditions or disease states, may require prolonged treatment involving multiple administrations.

Suitable doses and dosage regimens can be determined by conventional range-finding techniques known to those of ordinary skill in the art. When administering an adenoviral vector composition, preferably about $10^6$ viral particles to about $10^{12}$ viral particles are delivered to the diseased tissue. In other words, an adenoviral vector composition can be administered that comprises an adenoviral vector concentration of from about $10^6$ particles/ml to about $10^{12}$ particles/ml (including all integers within the range of about $10^6$ particles/ml to about $10^{12}$ particles/ml), preferably from about $10^{10}$ particles/ml to about $10^{12}$ particles/ml, and will typically involve the direct administration of from about 0.1 µl to about 100 µl of such an adenoviral vector composition to each affected tissue. Of course, other routes of administration may require smaller or larger doses to achieve a therapeutic effect. Any necessary variations in dosages and routes of administration can be determined by the ordinarily skilled artisan using routine techniques known in the art.

In some embodiments, it is advantageous to administer two or more (i.e., multiple) doses of the adenoviral vector composition. The invention provides for multiple applications of the adenoviral vector composition to selectively kill cells within which the adenoviral vector can replicate, thereby prophylactically or therapeutically treating a particular disease state associated with these abnormal cells. For example, at least two applications of an adenoviral vector composition can be administered to the same tissue. Preferably, the cell(s) is contacted with two applications or more of the adenoviral vector composition via direct administration to the desired tissue within about 30 days or more. More preferably, two or more applications are administered to cells of the same tissue within about 90 days or more. However, three, four, five, six, or more doses can be administered in any time frame (e.g., 2, 7, 10, 14, 21, 28, 35, 42, 49, 56, 63, 70, 77, 85 or more days between doses) so long as the desired therapeutic effect is achieved.

The adenoviral vector composition can be introduced ex vivo into cells, previously removed from the mammal, and exposed to the adenoviral vector composition, although this is less preferred. Such transduced autologous or homologous host cells, reintroduced into the mammal or human, will express directly the non-native nucleic acid sequence in vivo following initiation of adenoviral DNA replication. One ex vivo therapeutic option involves the encapsidation of infected cells into a biocompatible capsule, which can be implanted into a particular tissue. Such cells need not be isolated from the patient, but can instead be isolated from another individual and implanted into the patient.

The inventive method also can involve the co-administration of other pharmaceutically active compounds. By "co-administration" is meant administration before, concurrently with, e.g., in combination with the adenoviral vector in the same formulation or in separate formulations, or after administration of the adenoviral vector composition as described above. For example, factors that control inflammation, such as ibuprofen or steroids, can be co-administered to reduce swelling and inflammation associated with administration of the adenoviral vector composition. Immunosuppressive agents can be co-administered to reduce inappropriate immune responses related to a disorder or the practice of the inventive method. Anti-angiogenic factors, such as soluble growth factor receptors, growth factor antagonists, i.e., angiotensin, and the like can also be co-administered, as well as can be neurotrophic factors. Similarly, vitamins and minerals, anti-oxidants, and micronutrients can be co-administered. Antibiotics, i.e., microbicides and fungicides, can be co-administered to reduce the risk of infection associated with a particular pathologic state.

Adenoviral vectors of the invention typically are propagated as viral stocks in a cell line (e.g., the 293 cell line ATCC #CRL 1573, American Type Culture Collection, Manassas, Va.; Graham et al., J. Gen. Virol, 36: 59 (1977)) which can provide E1a function, E1b function, or both E1a and E1b functions, respectively, in trans to support replication and formation of infectious mutant virions. Complementation of other replication-essential gene functions, such as those of the E4 region, can be provided by, for example, a helper virus, which can be co-transfected with an adenoviral vector of the invention into a particular cell line to allow replication of the adenoviral vector or by way of other cell lines such as described in International Patent Application WO 95/34671.

EXAMPLE

This example further illustrates the invention but, of course, should not be construed as in any way limiting its scope. This example illustrates the construction of an adenoviral vector of the invention.

pAd70-100 is a plasmid comprising wild-type Ad5 sequence from map unit 70 to map unit 100. pAd70-100 was converted to pAd70-100dlE3 by deleting the majority of the E3 transcription unit.

The deletion of the E3 region was accomplished as follows. pAd70-100 was partially restriction digested with the restriction enzyme Mun I followed by insertion of a linker having a Mun I and Bam HI site. The insertion of the linker allowed for the selection of pAd70-100+BamHI, by screening for clones with a Bam HI site only at 91 map units. E3 sequences from 78.6 to 85.9 map units were deleted, and a unique Pac I site was inserted by PCR amplification of DNA from map units 76.2 to 78.6 (hereinafter "fragment 1") and 85.9 to 87 (hereinafter "fragment 2"). Pac I sites were present at the 78.6 and 85.9 ends of fragments 1 and 2, respectively. Fragment 1 was digested with Srf I and Pac I, fragment 2 was digested with Pac I and Sph I, and pAd70-100+BamHI with Srf I and Sph I. Ligation of the fragments yielded the plasmid pAd70-100dlE3.

pAd70-100dlE3 was used to generate a right-end adenoviral genome comprising a MLTU containing a terminal exon comprising a non-native nucleic acid sequence encoding a protein that does not contribute to the adenoviral vector entry into a host cell, in addition to a 5' splice acceptor DNA sequence and 3' polyA signal sequence. To accomplish this, a linker containing a Pac I site was inserted into pAd70-100dlE3 at the unique Bam HI site. pAd70-100dlE3 was then used to generate pAd70-100dlE3.IL-2 by PCR amplifying the IL-2 gene from a cDNA template with Pac I and Bam HI restriction enzyme sites inserted upstream and downstream of the IL-2 coding sequence. The resulting IL-2 PCR product was then inserted downstream of the coding region of the L5 polyA signal sequence in an area that does not perturb the E4 transcript or open reading frames (which is expressed from the opposite strand of the genome downstream of the fiber region). This resulted in a right-end adenoviral genome containing a MLTU comprising a terminal exon comprising a non-native nucleic acid sequence encoding IL-2.

The above-described right-end adenoviral genome was then co-transfected into 293 cells with left-end adenoviral arms, some of which included deletions of the E1a region (i.e., deletions in the CR1 and/or CR2 domain) and/or the E1b region (i.e., deletions in the 55 kd protein). The resultant adenoviral vectors contained a MLTU comprising a terminal exon comprising a non-native nucleic acid sequence encoding IL-2 located downstream of the L5 region of the adenoviral genome such that IL-2 is selectively expressed in cells within which the adenoviral vector can replicate. In that respect, adenoviral vectors were generated to selectively replicate and subsequently express IL-2 in $Rb^{(-)}$, $p53^{(-)}$, and $Rb^{(-)}p53^{(-)}$ cells.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An adenoviral vector comprising an adenoviral major late transcription unit (MLTU), wherein a terminal exon is inserted into the MLTU and wherein the terminal exon comprises (a) a 5' slice acceptor DNA sequence element, (b) a non-native nucleic acid sequence encoding a protein that does not contribute to the adenoviral vector entry into a host cell, and (c) a 3' polyadenylation (polyA) signal sequence, such that the non-native nucleic acid sequence is selectively expressed in cells within which the adenoviral vector can replicate.

2. The adenoviral vector of claim 1, wherein the adenoviral vector is deficient in one or more replication-essential gene functions.

3. The adenoviral vector of claim 2, wherein the adenoviral vector is deficient in one or more replication-essential gene functions of the E1a region, the E4b region, and/or the E4 region.

4. The adenoviral vector of claim 3, wherein the adenoviral vector is deficient in the one or more replication-essential gene functions of the E1b region but retains one or more replication-essential gene functions of the E1a region.

5. The adenoviral vector of claim 4, wherein the adenoviral vector selectively replicates in cells lacking a functional p53 gene product.

6. The adenoviral vector of claim 3, wherein the adenoviral vector is deficient in the one or more replication-essential gene functions of the E1a region but retains one or more replication-essential gene functions of the E1b region.

7. The adenoviral vector of claim 6, wherein the adenoviral vector selectively replicates in cells lacking a functional retinoblastoma (Rb) gene product.

8. The adenoviral vector of claim 1, wherein the terminal exon is inserted into the MLTU downstream of a L1 terminal exon.

9. The adenoviral vector of claim 8, wherein the terminal exon is inserted into the MLTU downstream of a L3 terminal exon.

10. The adenoviral vector of claim 1, wherein the non-native nucleic acid sequence encodes a protein which causes an immune response to be initiated against the cells within which the adenoviral vector can replicate when the cells are in a mammal.

11. The adenoviral vector of claim 10, wherein the non-native nucleic acid sequence encodes a cytokine.

12. The adenoviral vector of claim 1, wherein the non-native nucleic acid sequence encodes a protein that is toxic to the cells within which the adenoviral vector replicates.

13. The adenoviral vector of claim 1, wherein the MLTU comprises an insertion of multiple terminal exons, each comprising from 5' to 3':
   (a) the 5' splice acceptor DNA sequence element,
   (b) the non-native nucleic acid sequence, and
   (c) the 3' polyA sequence.

14. The adenoviral vector of claim 1, wherein the terminal exon comprises, from 5' to 3':
   (a) the 5' splice acceptor DNA sequence element,
   (b) an adenoviral nucleic acid sequence,
   (c) an internal ribosomal entry site (IRES),
   (d) the non-native nucleic acid sequence, and
   (e) the 3' polyA sequence,
   such that both the adenoviral and non-native nucleic acid sequences are expressed in cells within which the adenoviral vector can replicate.

15. The adenoviral vector of claim 14, wherein the adenoviral nucleic acid sequence encodes a fiber protein.

16. The adenoviral vector of claim 1, wherein the MLTU comprises an insertion of multiple terminal exons, each comprising from 5' to 3':
   (a) the 5' splice acceptor DNA sequence element,
   (b) an adenoviral nucleic acid sequence,
   (c) an IRES,
   (d) the non-native nucleic acid sequence, and
   (e) the 3' polyA sequence,
   such that both the adenoviral and non-native nucleic acid sequences are expressed in cells within which the adenoviral vector can replicate.

17. An adenoviral vector composition comprising the adenoviral vector of claim 1 and a carrier.

18. An adenoviral vector composition comprising the adenoviral vector of claim 2 and a carrier.

19. An adenoviral vector composition comprising the adenoviral vector of claim 3 and a carrier.

* * * * *